May 18, 1943. J. H. NICOLAS Plant Pat. 586
ROSE
Filed Oct. 27, 1942
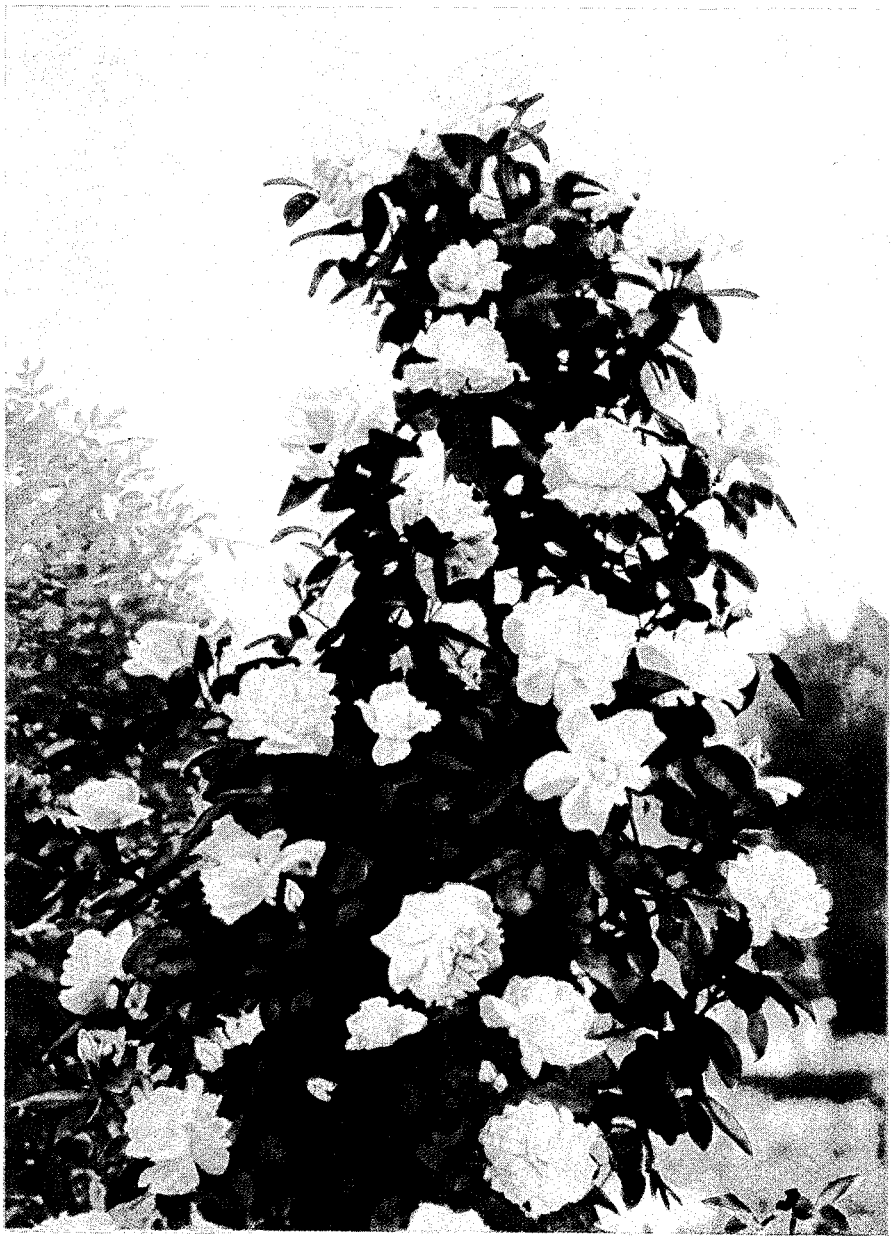
Inventor
Jean H. Nicolas,
By Fannie Nicolas,
Administratrix of the Estate
of Jean H. Nicolas, deceased
By Robb & Robb
Attorneys Patented May 18, 1943

Plant Pat. 586

UNITED STATES PATENT OFFICE

586

ROSE

Jean H. Nicolas, deceased, late of Newark, N. Y., by Fannie Nicolas, administratrix, Newark, N. Y., assignor to Jackson & Perkins Company, Newark, N. Y.

Application October 27, 1942, Serial No. 463,526

1 Claim. (Cl. 47—61)

The present invention relates to a new and distinct variety of rose plant of the climber type, originated from the cross of an unnamed everblooming seedling and an unnamed yellow seedling.

The unnamed everblooming seedling above referred to blooms in clusters of four or five flowers having a light pink-toned yellow shade, while the pollen parent is a yellow seedling which has attractive large flowers but is sparse in blooming and does not repeat.

This new variety possesses numerous features distinguishing it from its parents and other known roses in its class among which may be mentioned the following:

(*a*) Its blooming habit of producing large numbers of golden-yellow pointed buds, flushed with red, on medium long stems, slow to open, and holding their graceful, high-centered form almost until the full-open stage.

(*b*) The habit of its buds of opening into large blooms averaging four and one-half to five inches in diameter and gradually lightening from the golden-yellow to a clear yellow color which it retains until the petals drop, with a red striping on the reverse of the petals resembling in form the shape of a check mark.

(*c*) The habit of the plant of establishing itself quickly and throwing out long, stout, blooming wood from basal shoots, with the canes growing to a height of eight to ten feet high and blooming freely the next year.

(*d*) Its habit of blooming over a long period of time, beginning early in the season and continuing with great prolificacy through June until after other large-flowered climbers have ended their blooming period.

(*e*) The shape of the flowers which flatten out at the final stage and disclose attractive stamens.

(*f*) The persistence and disease resistance of the leathery foliage, quite unusual in climbers.

It may be noted in addition to the foregoing that the large hybrid-tea-like flowers come in clusters of four to six, almost completely covering the plant for from three to six weeks in early summer according to the locality in which this variety is grown.

Asexual reproduction of this new variety shows the foregoing characteristics come true to form and are established.

The following is a detail description of the new variety, the color terminology being in accord with Ridgway's Color Standard:

Parentage:

Seedling.

*Seed parent.*—Unnamed everblooming seedling.

*Pollen parent.*—Unnamed yellow seedling.

Classification:

*Botanic and commercial.*—Climber.

*Flower*

Observations made at Newark, New York, in the afternoon of July 11, 1942.

Blooming habit. Blooms from early into mid-season.

Bud:

*Size.*—Medium.

*Form.*—Long.

Is not affected by wet or hot weather.

*Color.*—When sepals first divide—Pale Viridine Yellow, Plate 5. When petals begin to unfurl—Empire Yellow, Plate 4, striped with Scarlet Red, Plate I.

When half blown: *Inside of petals*—Pinard Yellow, Plate 4. *Reverse of petals*—Empire Yellow, Plate 4, striped with Scarlet Red, Plate I, on the center vein which returns half way down on the righthand side of the petal giving the effect of a check mark.

*Sepals.*—Branched, "hood" above bud. Curl back when petals begin to unfurl. *Color.*—Biscay Green, Plate 17.

*Calyx.*—Shape—pear. Size—large. Aspect—smooth. Color—Light Elm Green, Plate 17.

*Peduncle.*—Length—medium. Aspect—smooth. Color—Parrot Green, Plate 6. Strength—erect; slender.

*Opening.*—Bud opens well. Is not affected by adverse conditions.

Bloom:

*Size.*—Large. Average size when fully expanded—4 inches.

*Borne.*—Singly.

*Stems.*—Medium length; normal.

*Form.*—When first open, flat, high center. Permanence—flattens but does not fold back.

*Petalage.*—Semi-single (two rows of petals). Number of petals under normal conditions—16 to 18.

*Color.*—Center of flower—Amber Yellow, Plate 16. Outer petals—Pinard Yellow, Plate 4. Base of petals (aiglet)—Lemon Chrome, Plate 4. Inside of petals—Empire Yellow, Plate 4. Reverse of petals—Pinard Yellow, Plate 4.

*Discoloration.*—General tonality at end of first day—Amber Yellow, Plate 4. Second day—Pinard Yellow, Plate 4. Third day—Pinard Yellow, Plate 4.

Petals:

*Texture.*—Leathery. Is not affected by wet or hot weather.

*Appearance.*—Inside—satiny. Outside—shiny.

*Form.*—Oval; notched.

*Arrangement.*—Regularly arranged shingle-like. Petaloids in center—few; medium size.

*Persistence.*—Drop off cleanly.

*Fragrance.*—Moderate. Nature—Sweet Briar.

*Lasting quality.*—On the plant—long. As cut flower—long.

Genital organs:

*Stamens, anthers.*—Medium size; many. Color—Light Cadmium, Plate 4. Arrangement—regular around styles.

*Stamens, filaments (threads).*—Medium length. Color—Bittersweet Orange, Plate 2.

*Pollen.*—Apricot Yellow, Plate 4.

*Styles.*—Bunched, uneven length; medium length; thin.

*Stigmas.*—Pale Lemon Yellow, Plate 4.

*Ovaries.*—All enclosed in calyx.

*Plant*

Form: Climber.

Growth: Vigorous; upright.

Foliage: 7 leaflets.

*Size.*—Medium.

*Quantity.*—Abundant.

*Color.*—*New foliage*—Upper side—Parrot Green, Plate 6; mid-rib Calliste Green, Plate 6; serration Madder Brown, Plate 13. Under side—Absinthe Green, Plate 31; serration Madder Brown, Plate 13. *Old foliage*—Upper side—Jade Green, Plate 31. Under side—Light Bice Green, Plate 17.

*Shape.*—Oval pointed.

*Texture.*—Upper side—leathery. Under side—rough. Ribs and veins—prominent.

*Edge.*—Serrated (saw toothed).

*Serration.*—Single; small.

*Rachis.*—Light Elm Green, Plate 17. Under side—prickles.

*Stipules.*—Medium length; bearded.

*Disease resistance.*—Resistant, as indicated by the fact that plants of this variety have been grown in test gardens where they are exposed to the normal ills of such environment and failed to acquire any of the common diseases.

Wood:

*New wood.*—Lettuce Green, Plate 5. Bark—smooth.

*Old wood.*—Cress Green, Plate 31. Bark—smooth.

Thorns: (Thorns are divided into thorns, prickles and short needles.)

*Thorns.*—On main stalks from base and on laterals from stalk—many. Form—narrow base; long; hooked downward. Color when young—base, Oxblood Red, Plate 1; tip end, Cosse Green, Plate 5. Position—irregular.

*Prickles.*—On main stalks and on laterals—few. Color—Citron Green, Plate 31.

*Short needles.*—On main stalks and on laterals—few.

What is claimed is:

A new and distinct variety of rose plant of the climber type characterized as to novelty by the large size and form of the blooms, particularly at its final stage of development, the prolificacy of the bloom and unusual length of the blooming period, the yellow coloring of the bloom flushed with red, and peculiar check-like striping of the petals, and the persistence and disease-resistant leathery foliage of the plant, substantially as shown and described.

FANNIE NICOLAS,
*Administratrix of the Estate of Jean H. Nicolas, Deceased.*